United States Patent
Bland et al.

(10) Patent No.: US 9,115,135 B2
(45) Date of Patent: *Aug. 25, 2015

(54) PROCESS FOR THE PREPARATION OF 2-AMINO-5,8-DIMETHOXY[1,2,4]TRIAZOLO[1,5-C]PYRIMIDINE FROM 4-AMINO-2,5-DIMETHOXYPYRIMIDINE

(71) Applicant: Dow AgroSciences LLC, Indianapolis, IN (US)

(72) Inventors: Douglas C. Bland, Midland, MI (US); Christopher T. Hamilton, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/023,498

(22) Filed: Sep. 11, 2013

(65) Prior Publication Data

US 2014/0081024 A1    Mar. 20, 2014

Related U.S. Application Data

(60) Provisional application No. 61/701,242, filed on Sep. 14, 2012.

(51) Int. Cl.
*C07D 487/00* (2006.01)
*C07D 487/04* (2006.01)

(52) U.S. Cl.
CPC .................................. *C07D 487/04* (2013.01)

(58) Field of Classification Search
None
See application file for complete search history.

(56) References Cited

U.S. PATENT DOCUMENTS 8,143,395 B2    3/2012    Bott et al.
8,338,596 B2 *  12/2012   Bott et al. ............... 544/263

* cited by examiner

*Primary Examiner* — Jeffrey H Murray
(74) *Attorney, Agent, or Firm* — Michael R. Asam

(57) ABSTRACT

5-Substituted-8-alkoxy[1,2,4]triazolo[1,5-c]pyrimidin-2-amines are manufactured from 4-amino-2,5-dialkoxypyrimidines in an improved process in which the generation of gaseous by-products is controlled by the continuous addition of hydroxylamine as a free base.

11 Claims, No Drawings

PROCESS FOR THE PREPARATION OF 2-AMINO-5,8-DIMETHOXY[1,2,4]TRIAZOLO[1,5-C]PYRIMIDINE FROM 4-AMINO-2,5-DIMETHOXYPYRIMIDINE

CROSS REFERENCE TO RELATED APPLICATIONS

This application claims the benefit of U.S. Provisional Patent Application Ser. No. 61/701,242 filed Sep. 14, 2012, the disclosure of which is expressly incorporated herein by reference.

BACKGROUND

Provided herein is an improved process for the preparation of 2-amino-5,8-dimethoxy[1,2,4]triazolo[1,5-c]pyrimidine from 4-amino-2,5-dimethoxypyrimidine.

U.S. Pat. No. 8,143,395 B2 describes a method to manufacture certain 2-amino-5,8-dialkoxy[1,2,4]triazolo[1,5-c] pyrimidines that avoids hydrazine and cyanogen halide. In this process a 4-amino-2,5-dialkoxypyrimidine is reacted with, for example, ethoxy carbonyl-isothiocyanate (S=C=N—CO$_2$Et) in a polar aprotic solvent to provide an ethyl[(2,5-dialkoxypyrimidin-4-yl)amino]carbonothioylcarbamate, which in turn is reacted with an hydroxylamine salt in the presence of a base to provide an ethyl[(2,5-dialkoxypyrimidin-4-yl)amino](hydroxyimino)methylcarbamate. Upon heating, this intermediate cyclizes via a series of reactions to provide the desired 2-amino-5,8-dialkoxy[1,2,4]triazolo[1,5-c]-pyrimidines. While the process described in U.S. Pat. No. 8,143,395 B2 eliminates the need for hydrazine and cyanogen halide, it introduces new challenges with respect to the generation of several equivalents of gaseous by-products. It would be desirable to have a more streamlined and safer process by which to produce 2-amino-5,8-dialkoxy[1,2,4]-triazolo[1,5-c]pyrimidines.

SUMMARY

Provided herein is an improved process for the preparation of 2-amino-5,8-dimethoxy[1,2,4]triazolo[1,5-c]pyrimidine from 4-amino-2,5-dimethoxypyrimidine. In some embodiments, 2-amino-5,8-dialkoxy[1,2,4]triazolo[1,5-c]pyrimidines of the formula (I),

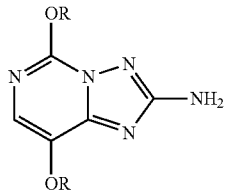

I in which
R represents C$_1$-C$_4$ alkyl
are prepared in a process which comprises:
i) contacting a 4-amino-2,5-dialkoxypyrimidine of the formula

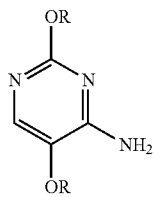

in which R is as previously defined
with a C$_1$-C$_4$ alkoxy carbonylisothiocyanate of the formula

S=C=N—C(O)OR in which R is as previously defined,
in a polar or nonpolar aprotic solvent at a temperature from about 60° C. to about 110° C. to provide a [(2,5-dialkoxypyrimidin-4-yl)amino]carbonothioylcarbamate of the formula

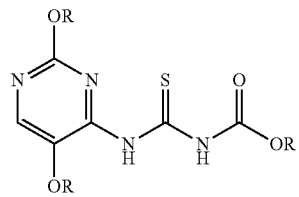

in which R is as previously defined; and
ii) continuously adding to the [(2,5-dialkoxypyrimidin-4-yl)amino]carbono-thioylcarbamate in the polar or nonpolar aprotic solvent an aqueous solution of hydroxylamine at a temperature from about 60° C. to about 110° C. to provide the 2-amino-5,8-dialkoxy[1,2,4]triazolo[1,5-c]pyrimidine.

DETAILED DESCRIPTION

The term alkyl and derivative terms such as alkoxy, as used herein refer to straight chain or branched chain groups. Typical alkyl groups are methyl, ethyl, propyl, 1-methylethyl, butyl, 1,1-dimethylethyl and 1-methylpropyl. Methyl and ethyl are often preferred.

The present invention concerns an improved process for the preparation of a 2-amino-5,8-dialkoxy[1,2,4]triazolo[1, 5-c]pyrimidine from 4-amino-2,5-dialkoxypyrimidine. It is particularly useful for the preparation of 2-amino-5,8-dimethoxy[1,2,4]triazolo[1,5-c]-pyrimidine from 4-amino-2,5-dimethoxypyrimidine.

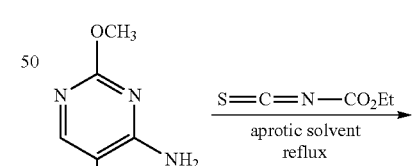

1

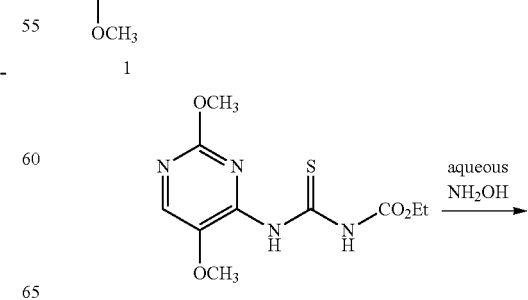

2

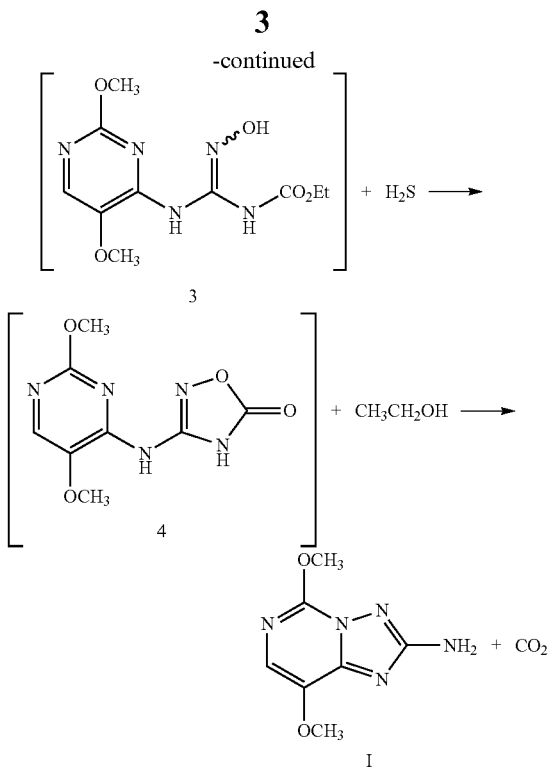

U.S. Pat. No. 8,143,395 B2 teaches that, in the first step of the reaction, the alkoxy carbonylisothiocyanate should be added to the 4-amino-2,5-dialkoxypyrimidine in a polar aprotic solvent, preferably acetonitrile or ethyl acetate, at a temperature from 0° C. to room temperature. It has now been found that the reaction of the alkoxy carbonylisothiocyanate need not be conducted at or below room temperature and that nonpolar aprotic solvents such as toluene perform just as well as polar aprotic solvents and offer advantages with respect to recovery and recycle.

Similarly, U.S. Pat. No. 8,143,395 B2 recommends using at least an equivalent of hydroxylamine, preferably as a salt, with a base (not uncommonly up to 4 equivalents each of hydroxylamine salt and base) at a temperature between 0° C. and 35° C., preferably at room temperature. The use of hydroxylamine as a salt with a base suggests the approach of frontloading the entire amount of hydroxylamine reagent. Low temperatures would be needed to control the release of gaseous by-products generated during the cascade of cyclization reactions. By continuously adding an aqueous solution of hydroxylamine as a free base, higher temperatures from about 60° C. to about 110° C. can be safely used and the release of gaseous by-products mitigated by the controlled addition of hydroxylamine.

Polar or nonpolar aprotic solvents include both aromatic and aliphatic hydrocarbons and halogenated hydrocarbons, esters, nitriles and amides.

The first step of the present invention (i) concerns the conversion of a 4-amino-2,5-dialkoxypyrimidine to a R2,5-dialkoxypyrimidin-4-yl)aminolcarbonothioylcarbamate.
This is accomplished using at least one equivalent and preferably a small excess of $C_1$-$C_4$ alkoxy carbonylisothiocyanate in a polar or a nonpolar aprotic solvent. In certain embodiments, the polar or nonpolar aprotic solvent is acetonitrile, ethyl acetate or toluene. The alkoxy carbonylisothiocyanate is added at a temperature from about ambient to about 110° C.; the mixture is then heated at a temperature from about 60° C. to about 110° C. In certain embodiments, the reaction mixture is heated to the reflux temperature of the solvent(s). In certain embodiments, the temperature is at least 60° C., at least 70° C., at least 80° C., at least 90° C., or at least 100° C. The product can be isolated by conventional techniques, such as by filtration of a precipitated or crystallized material, but is generally used as is in the next step.

In certain embodiments, the 4-amino-2,5-dialkoxypyrimidine is dissolved or suspended in the polar or nonpolar aprotic solvent and then treated with the appropriate amount of the $C_1$-$C_4$ alkoxy carbonylisothiocyanate. After heating to reflux, the reaction mixture can be cooled for storage or used immediately for step (ii).

The second step of the present invention (ii) concerns the conversion of the [2,5-dialkoxypyrimidin-4-yl)amino]carbonothioylcarbamate to the 2-amino-5,8-dimethoxy[1,2,4]-triazolo[1,5-c]pyrimidine. This is accomplished using at least an equivalent, and in certain embodiments, a small excess, of hydroxylamine as the free base. The aqueous solution of hydroxylamine is continuously added to the mixture of [2,5-dialkoxypyrimidin-4-yl)amino]carbonothioyl-carbamate in a polar or a nonpolar aprotic solvent from step (i) at a temperature from about 60° C. to about 110° C. at a rate slow enough to safely handle the release of gaseous by-products generated during the cascade of cyclization reactions leading to the 2-amino-5,8-dialkoxy[1,2,4]triazolo[1,5-c]pyrimidine. In certain embodiments, the temperature is at least 60° C., at least 70° C., at least 80° C., at least 90° C., or at least 100° C. The reaction mixture is cooled and can be optionally treated with sodium sulfite as a deodorizer. In some embodiments, the product is isolated by conventional techniques, such as collection by filtration and drying.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

All reagents described were obtained commercially and used without additional purification.

Example 1

Preparation of 2-amino-5,8-dimethoxy[1,2,4]triazolo [1,5-c]pyrimidine (Ia)

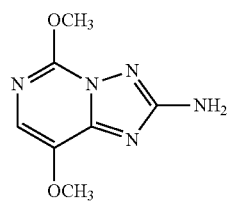

To a 700 milliliter (mL) jacketed vessel equipped with a mechanical stirrer, a dual pH/temperature probe, a nitrogen inlet, and a reflux condenser was added sequentially 19.4 grams (g; 0.125 moles (mol)) of 4-amino-2,5-dimethoxypyrimidine followed by 151 g (1.717 mol) of ethyl acetate. The reaction mixture was heated to reflux (~80° C.) and then 18.7 g (0.143 mol) of ethoxy carbonylisothiocyanate was continuously added via addition funnel over a 22 minute (min) period. The addition funnel was rinsed with 1.8 g of ethyl acetate and then the reaction mixture was heated at reflux for 9 hours (h). The reaction mixture was cooled to 25° C. and allowed to stand overnight. The mixture was heated to 60° C. and then 100 g (5.500 mol) of deionized water was added to the mixture. After heating to reflux (~71° C.), 9.4 g (0.142 mol) of a 50 weight percent (wt %) aqueous hydroxylamine solution was continuously added over a 1 h period. During the course of the amine addition, the reaction pH rose from 4.00 to 6.60. The reaction mixture was then heated an additional 3 h during which time the reaction pH naturally lowered to 6.30. To this reaction mixture was added a solution of 4.5 g (0.036 mol) of sodium sulfite in 20 g (1.110 mol) of deionized water over an 8 min period. The reaction pH rose from 6.30 to 7.44 during the sodium sulfite addition. The reaction mixture was then cooled to ambient temperature and allowed to stand overnight. The reaction mixture was suction filtered through a medium coarse fritted glass funnel (filtration time less than 2.0 min), and then the reaction vessel was washed with 150 g of deionized water and this rinse was used to wash the isolated product cake. A final displacement wash with 30 g of fresh deionized water was performed and the product was partially dried by suction for 3.5 h to afford 18.01 g of 2-amino-5,8-dimethoxy[1,2,4]triazolo[1,5-c]pyrimidine as a light cream colored wet cake. NMR analysis (using benzyl acetate as an internal standard) indicated a 91.6% purity which corresponds to a 67.5% yield. $^1$H NMR (DMSO-$d_6$, 400 MHz) δ 3.89 (s, 3H), 4.06 (s, 3H), 6.27 (br s, 2H), 7.47 (s, 1H); $^{13}$C NMR (DMSO-$d_6$, 100 MHz) δ 55.37, 57.03, 123.06, 138.59, 143.72, 148.49, 166.01.

Example 2

Preparation of 2-amino-5,8-dimethoxy[1,2,4]triazolo[1,5-c]pyrimidine (Ia)

To a 700 mL jacketed vessel equipped with a mechanical stirrer, a dual pH/temperature probe, a nitrogen inlet, and a reflux condenser was added sequentially 19.4 g (0.125 mol) of 4-amino-2,5-dimethoxypyrimidine followed by 151 g (1.717 mol) of ethyl acetate. The reaction mixture was heated to reflux (~80° C.) and then 18.7 g (0.143 mol) of ethoxy carbonylisothiocyanate was continuously added via addition funnel over an 8 min period. The addition funnel was rinsed with 1.8 g of ethyl acetate and then the reaction mixture was heated at reflux for 9 h. The reaction mixture was cooled to 25° C. and allowed to stand overnight. The mixture was heated to 60° C. and then 100 g (5.50 mol) of deionized water was added to the mixture. After heating to reflux (~71° C.), 9.4 g (0.142 mol) of a 50 wt % aqueous hydroxylamine solution was continuously added over a 46 min period. During the course of the amine addition, the reaction pH rose from 4.20 to 6.35. The reaction mixture was then heated an additional 3 h during which time the reaction pH naturally lowered to 6.30. To this reaction mixture was added a solution of 4.5 g (0.036 mol) of sodium sulfite in 20 g (1.110 mol) of deionized water over a 6 min period. The reaction pH rose from 6.35 to 7.51 during the sodium sulfite addition. The reaction mixture was then cooled to 18° C. and allowed to stir an additional 30 min at this temperature. The reaction mixture was suction filtered through a medium coarse fritted glass funnel (filtration time less than 2.0 min), and then the reaction vessel was washed with 30 g of deionized water and this rinse was used to wash the isolated product cake. A final displacement wash with 30 g of fresh deionized water was performed and the product was partially dried by suction for 30 min and then allowed to dry overnight under a gentle stream of nitrogen to afford 19.1 g of 2-amino-5,8-dimethoxy[1,2,4]triazolo[1,5-c]pyrimidine as a light cream colored wet cake. NMR analysis (using benzyl acetate as an internal standard) indicated a 88.25% purity of 2-amino-5,8-dimethoxy[1,2,4]triazolo[1,5-c]pyrimidine active which corresponds to a 69.1% yield.

Example 3

Preparation of 2-amino-5,8-dimethoxy[1,2,4]triazolo[1,5-c]pyrimidine (Ia)

To a 700 mL jacketed vessel equipped with a mechanical stirrer, a dual pH/temperature probe, a nitrogen inlet, and a reflux condenser was added sequentially 19.4 g (0.125 mol) of 4-amino-2,5-dimethoxypyrimidine followed by 151 g (1.639 mol) of toluene. The reaction was heated to gentle reflux (~80° C.) and then 19.24 g (0.144 mol) of 98% ethoxy carbonylisothiocyanate was added, and the reaction mixture was heated at gentle reflux (89° C.) for 7 h. The reaction mixture was cooled to 26° C. and allowed to stand overnight. The mixture was heated to 60° C. and then 100 g (5.500 mol) of deionized water was added to the mixture. After heating to reflux (~69° C.), 9.6 g (0.145 mol) of a 50 wt % aqueous hydroxylamine solution was continuously added over a 1 h period. During the course of the amine addition, the reaction pH rose from 4.00 to 6.67. After completing addition of hydroxylamine, the reaction mixture was heated to 77° C. and then stirred an additional 3 h during which time the reaction pH naturally raised to 7.42. To this reaction mixture was added a solution of 4.5 g (0.036 mol) of sodium sulfite in 20 g (1.110 mol) of deionized water over a one min period. The reaction pH rose from 7.34 to 7.81 during the sodium sulfite addition. The reaction mixture was stirred an additional 1 h at 77° C. and then cooled to ambient temperature and allowed to stand overnight. The reaction mixture was suction filtered through a medium coarse fritted glass funnel (filtration time was 43 min), and then the reaction vessel was washed with 30 g of deionized water and this rinse was used to wash the isolated product cake. A final displacement wash with 30 g of fresh deionized water was performed and the product was dried to afford 19.62 g of 2-amino-5,8-dimethoxy[1,2,4]triazolo[1,5-c]pyrimidine as a light cream colored solid. NMR analysis (using benzyl acetate as an internal standard) indicated an 83.3% purity of 2-amino-5,8-dimethoxy[1,2,4]triazolo[1,5-c]pyrimidine active which corresponds to a 67.0% yield.

Example 4

Preparation of 2-amino-5,8-dimethoxy[1,2,4]triazolo[1,5-c]pyrimidine (Ia)

To a 700 mL jacketed vessel equipped with a mechanical stirrer, a dual pH/temperature probe, a nitrogen inlet, and a reflux condenser was added sequentially 27.9 g (0.180 mol) of 4-amino-2,5-dimethoxypyrimidine followed by 165.4 g (0.207 mol) of 16.4 wt % ethoxy carbonylisothiocyanate solution in toluene. The reaction mixture was heated to gentle reflux (87° C.) for 7 h at which time liquid chromatographic (LC) analysis indicated ~95% conversion of starting 4-amino-2,5-dimethoxypyrimidine. The reaction mixture was cooled to 27° C. and allowed to stand overnight. The mixture was heated to 40° C. and then 114.2 g (6.34 mol) of deionized water was added to the mixture. After heating to reflux (~68° C.), 14.3 g (0.217 mol) of a 50 wt % aqueous hydroxylamine solution was continuously added over a 2 h 15 min period via a peristaltic pump. During the course of the amine addition, the reaction pH rose from 4.44 to 6.95. After complete addition of hydroxylamine, the pump line was flushed with 4.8 g (0.266 mol) of deionized water, the reaction mixture was heated to 81° C., and then stirred an additional 3 h during which time the reaction pH naturally raised to 7.40. The reaction mixture was cooled to ambient temperature (26° C.). The reaction mixture was then suction transferred into a temporary holding vessel. The reactor was washed with two 30 g portions of water. These water washes were combined with the reaction mixture. The combined mixture was suctioned filtered through a coarse Buchner funnel (filtration time about 30 seconds), and the filtrate was collected and filtered a second time through the cake. A final displacement cake wash with ~40 g of methanol was performed and the product was dried at 60° C. under vacuum (~<10 mm Hg; 1333 Pa) to afford 25.37 g of 2-amino-5,8-dimethoxy[1,2,4]triazolo[1,5-c]pyrimidine as a light cream colored solid. NMR analysis (using benzyl acetate as an internal standard) indicated an 97.3% purity of 2-amino-5,8-dimethoxy[1,2,4]triazolo[1,5-c]pyrimidine active which corresponds to a 70.4% yield.

What is claimed is:

1. A process for the preparation of 2-amino-5,8-dialkoxy[1,2,4]triazolo[1,5-c]-pyrimidines of the formula (I),

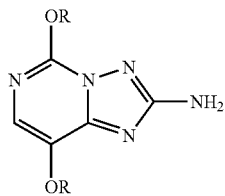

I in which R is $C_1$-$C_4$ alkyl comprising continuously adding to a [(2,5-dialkoxypyrimidin-4-yl)amino]carbono-thioylcarbamate of the following formula:

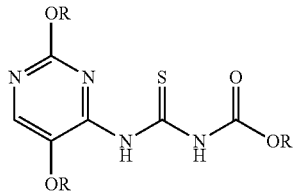

in which R is as previously defined in a polar or nonpolar aprotic solvent an aqueous solution of hydroxylamine free base at a temperature from about 60° C. to about 110° C. at a rate slow enough to safely handle the release of gaseous by-products.

2. The process of claim 1, wherein R is $CH_3$.

3. The process of claim 1, wherein the aprotic solvent is nonpolar.

4. The process of claim 1, wherein the aprotic solvent is toluene.

5. The process of claim 1, wherein said temperature is at least 80° C.

6. The process of claim 1, wherein the [(2,5-dialkoxypyrimidin-4-yl)amino]carbono-thioylcarbamate is formed by contacting a 4-amino-2,5-dialkoxypyrimidine of the formula

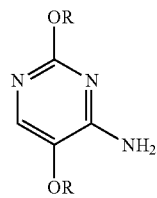

in which R is as previously defined with a $C_1$-$C_4$ alkoxy carbonylisothiocyanate of the formula

S=C=N—C(O)OR wherein R is as previously defined, in a polar or nonpolar aprotic solvent at a temperature from about 60° C. to about 110° C.

7. The process of claim 6, wherein R represents $CH_3$.

8. The process of claim 6, wherein the aprotic solvent is nonpolar.

9. The process of claim 6, wherein the aprotic solvent is toluene.

10. The process of claim 6, wherein the temperature of step (i) and (ii) is at least 60° C.

11. The process of claim 6, wherein the temperature of step (i) and (ii) is at least 80° C.

* * * * *